United States Patent [19]

Fisher et al.

[11] Patent Number: 4,819,477
[45] Date of Patent: Apr. 11, 1989

[54] METHOD AND APPARATUS FOR TRACE SAMPLE COLLECTION

[75] Inventors: William H. Fisher, Thornhill; William R. Stott, Aurora; Bruce A. Thomson, Etobicoke; Adam Weisz-Margulescu, Thornhill, all of Canada

[73] Assignee: MDS Health Group Limited, Etobicoke, Canada

[21] Appl. No.: 18,637

[22] Filed: Feb. 25, 1987

[30] Foreign Application Priority Data

Feb. 27, 1986 [CA] Canada .................................. 502923

[51] Int. Cl.4 ...................... G01N 1/22; G01N 31/06
[52] U.S. Cl. ............................................. 73/23; 73/28
[58] Field of Search ............... 73/23, 23.1, 863.21, 73/863.11, 863.12, 863.23, 863.25, 28; 422/88, 93; 55/179, 67; 204/24

[56] References Cited

U.S. PATENT DOCUMENTS

| | | | |
|---|---|---|---|
| 2,112,304 | 3/1938 | Rhed | 73/28 |
| 2,640,789 | 6/1953 | Hausner | 427/247 |
| 3,338,087 | 8/1967 | Moberg et al. | 73/23 |
| 3,458,973 | 8/1969 | Spencer et al. | 55/179 |
| 3,765,247 | 10/1973 | Riggs | 73/863.23 |
| 3,769,837 | 11/1973 | Kraus et al. | 73/23 |
| 3,897,679 | 8/1975 | Guild | 73/23.1 |
| 3,925,022 | 12/1975 | Showalter | 422/88 |
| 4,243,631 | 1/1981 | Ryerson | 73/27 R |
| 4,426,214 | 1/1984 | Vandrish | 73/218 |
| 4,469,918 | 2/1986 | Morssinkhof | 204/24 |
| 4,569,912 | 2/1986 | Moore et al. | 422/88 |
| 4,580,440 | 4/1986 | Reid et al. | 73/23 |
| 4,715,055 | 12/1987 | Devine, Jr. | 378/144 |

Primary Examiner—Stewart J. Levy
Assistant Examiner—Hezron E. Williams
Attorney, Agent, or Firm—Rogers, Bereskin & Parr

[57] ABSTRACT

A disposable plastic cartridge contains three fine lightweight wire mesh collectors, each of phosphor bronze. One collector has an oxidized surface for collecting drug particulates. The other two have surfaces electroplated with zinc to form a rough multi-fissured surface for trapping low volatility vapors. In use, a portion of a warm sample air stream is chilled and passed through the collectors in parallel for sample collection. Simultaneously part of the sample air stream by-passes the chiller and is fed directly into a mass analyzer for real time analysis. Next, both collection and real time analysis are terminated, and each collector is desorbed in sequence with a pulse of hot air which flows into the mass analyzer for sequential analysis.

27 Claims, 8 Drawing Sheets

METHOD AND APPARATUS FOR TRACE SAMPLE COLLECTION

FIELD OF THE INVENTION

This invention relates to method and apparatus for detecting trace substances in air. Such substances are typically compounds such as drugs, explosives, and other illicit substances.

BACKGROUND OF THE INVENTION

The detection of trace substances in air has many applications. An important application is the detection of substances which are being improperly carried by travellers or in containers, e.g. drugs, explosives or alcohol. It has been discovered, as disclosed in U.S. patent application Ser. No. 631,953 (now U.S. Pat. No. 4,580,440) of British Aerospace Public Limited Company, that many of such substances can be detected by collecting particulates which are emitted of such substances, and then analyzing the particulates. However the present inventors have discovered that the substances are often difficult to collect, and that special techniques are required to collect particulates and to collect vapours of low volatility. High efficiency collection is important because of the very low concentrations of the trace substances which are usually present.

BRIEF SUMMARY OF INVENTION

The present invention in one aspect is therefore concerned with method and apparatus for improved collection of particulates and low volatility vapours of trace substances which are to be detected. In one of its aspects the invention provides apparatus for collecting trace substances to be analyzed, comprising inlet means for receiving a stream of warm gas containing particulates and low volatility vapours of said trace substances, collection means connected to said inlet means for collecting said trace substances, and cooling means located between said inlet means and said collection means for cooling said warm air flowing from said inlet means to said collection means, thereby to increase the efficiency of collection of said collection means.

In another aspect the invention provides apparatus for analyzing trace substances, comprising:

(a) inlet means for receiving inlet air containing said trace substances, (b) first and second collectors each of different selectivity than the other, (c) means for directing at least a portion of said inlet air through both said first and second collectors in parallel, for said first and second collectors each simultaneously to collect at least some of said trace substances, (d) analyzer means, (e) and means for first releasing and transporting to said analyzer means the substances collected by said first collector, and thereafter releasing and transporting to said analyzer means the substances collected by said second collector.

In a further aspect the invention provides a disposable cartridge for collecting trace substances to be analyzed, said cartridge comprising at least two collectors therein, each collector being formed from a lightweight wire mesh of low thermal mass, a body supporting and retaining said collectors in spaced apart relationship from each other, said body being formed of plastic of low thermal conductivity, said collectors providing at least two channels of different selectivity from each other for simultaneous sample collection.

In another aspect the invention provides collection means for collecting particulates of trace substances, said collection means comprising a lightweight fine metal mesh, said metal mesh having an oxidized surface to decrease the reactivity thereof.

In another aspect the invention provides collection means for collecting low volatility vapours of trace substances of interest, said collection means comprising a lightweight fine mesh of a first metal, said mesh being of low thermal mass, said mesh having a second metal electroplated thereon to form a rough fissure-filled surface.

BRIEF DESCRIPTION OF THE DRAWINGS

The invention will be described in more detail with reference to the accompanying drawings, in which.

DETAILED DESCRIPTION OF PREFERRED EMBODIMENTS

The invention will be described primarily with reference to detection of drugs and explosives. These are largely compounds of medium to high molecular weight. It is found that some such compounds (particularly drugs such as heroin) are seen mainly in particle form. Others appear in the form of both particulates and vapours of low volatility, both of which can be collected. Still other compounds, e.g. solvents associated with such compounds, are of such high volatility that they cannot easily be collected and are best analyzed in real time.

Figure 1:
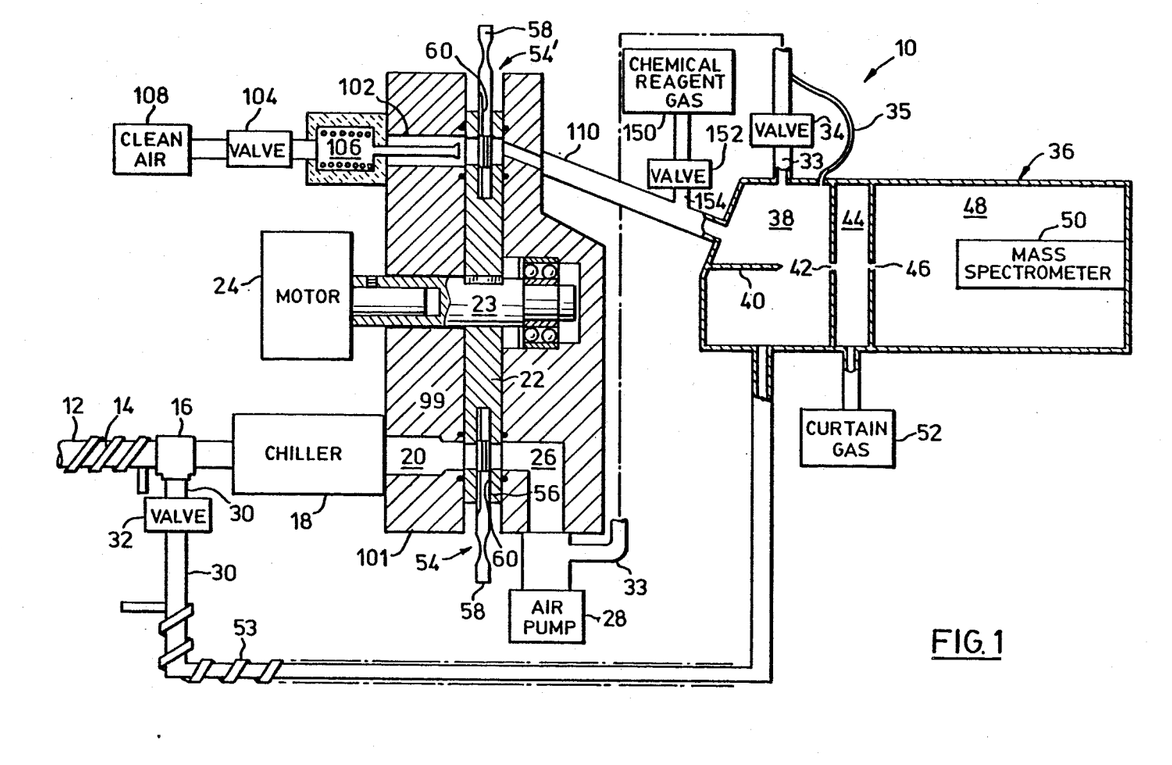
FIG. 1 is a diagrammatic view of apparatus according to the invention.

To analyze air which may contain any or all of such compounds, collection and analysis apparatus is provided as generally indicated at 10 in FIG. 1. The apparatus 10 includes an air inlet conduit 12 leading from a sample location from which air is to be collected. The sample location may for example be a freight container from which air is exhausted, to detect the presence of drugs or explosives therein, or it may be an airport location such as one where luggage is being examined, or where passengers are being scrutinized.

As explained in the above mentioned U.S. patent application, the conduit 12 should be reasonably short and free of sharp bends. In addition the conduit 12 is preferably heated, by heater element 14 wrapped therearound, so that the air therein is at a temperature of about 45° C. The heating reduces the likelihood that low volatility vapours will adhere to the walls of the conduit 12 but is not sufficient to vaporize particulates of interest or to drive most adsorbed vapours from the particulates.

The conduit 12 is directed through a T-fitting 16 into a chiller 18 and then through a conduit 20 into a circular disc 22. The disc 22 is rotatably mounted on a central axle 23 and can be manually turned or can be driven by a stepping motor 24. On the other side of the rotating disc 22, a conduit 26 continues to an air pump diagrammatically indicated at 28.

A bypass conduit 30 leaves the T-fitting 16 and is directed to a solenoid valve 32. From the valve 32 the conduit 30 leads into a mass analyzer 36 such as that sold by Sciex Division of MDS Health Group Limited of Thornhill, Ontario under its trade mark TAGA ®. The analyzer 36 is shown diagrammatically and includes an inlet section 38 which includes an ionizing source such as a corona discharge needle 40 which provides a corona discharge to ionize trace substances of interest. The resultant ions are then directed by an electric field through an orifice 42 into a gas curtain chamber 44 and then through another orifice 46 into a vacuum chamber 48. The ions are then directed by a lens (not shown) into a mass spectrometer 50 which provides an analysis of the ions.

The inlet section 38 includes an outlet 33 operated by a solenoid valve 34, and a permanent small outlet conduit 35 (typically 1/16" inner diameter) both leading to the inlet of air pump 28 for a purpose to be described.

The gas curtain chamber 44, described in U.S. Pat. No. 4,023,398 issued on May 13, 1977 to J. B. French et al, is connected to a source 52 of an inert curtain gas (such as argon) which effuses from orifice 42 into inlet section 38, i.e. countercurrent to the flow of ions into the orifice 42. The curtain gas thus prevents particulates from entering and clogging the orifices 42, 46 and allows only the ions (but none of the inlet air) to travel into the vacuum chamber 48. The curtain gas enters the vacuum chamber 48 and may be cryopumped, or pumped by an ordinary vacuum pump (not shown), to establish a vacuum in the chamber 48.

When air from a location of interest is to be analyzed, part of the air flows from conduit 12 through the bypass conduit 30 and into the analyzer 36 for real time analysis. Bypass conduit 30 is heated, typically to a wall temperature of about 100° C., by heater 53. Typically the bypass air volume is about 10% of the air from conduit 12. The remainder of the air from conduit 12 flows through the chiller 18 (whose function will be explained shortly), into the disc 22, and through a collection cartridge 54 (to be described) which is plugged into a slot 56 in the edge of the disc 22. The cartridge 54 collects particles, and vapours of low to medium volatility, from the air passing therethrough. These collected compounds can then be analyzed, preferably immediately after the real time analysis of volatile vapours which is occurring during the collection process.

Figure 2:
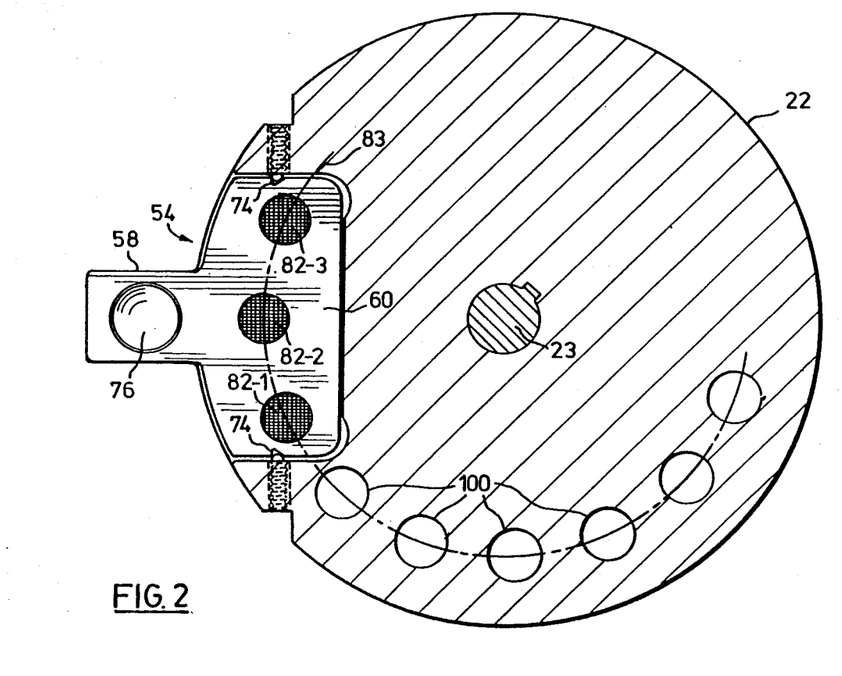
FIG. 2 is a plan sectional view of a disc for use with the FIG. 1 apparatus, with a cartridge inserted therein.
Figures 3, 4:
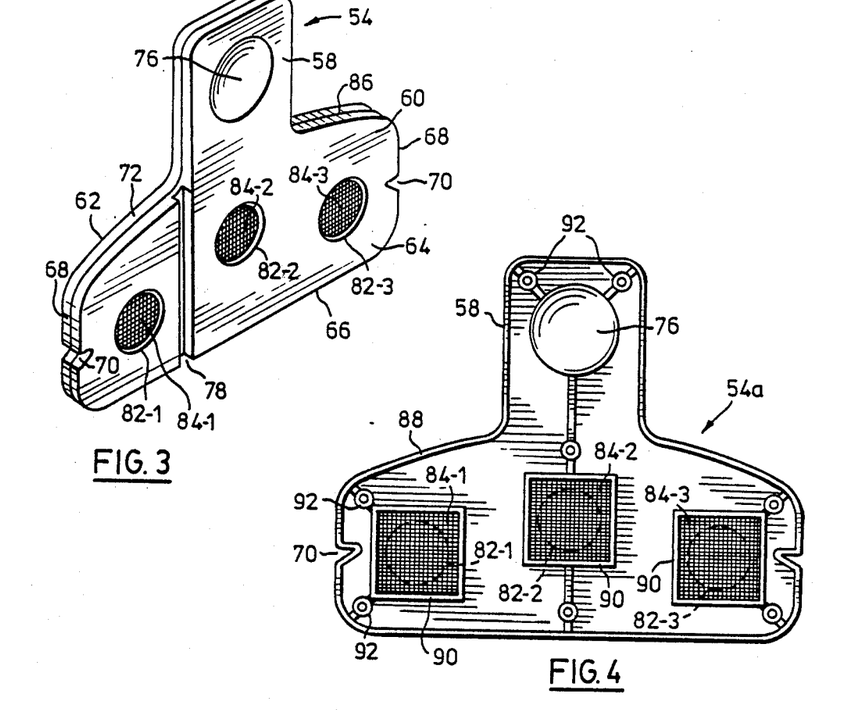
FIG. 3 is a perspective view of a cartridge for use with the disc of FIG. 2.
FIG. 4 is a plan view of one half of the cartridge of FIG. 3.
Figure 5:
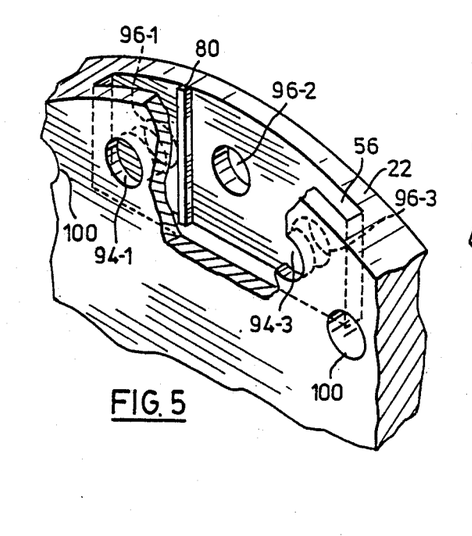
FIG. 5 is a perspective broken away view of part of the disc of FIG. 2.

The cartridge 54 is best shown in FIGS. 2, 3 and 4 and is generally T-shaped in form, having a projecting handle 58 and a body 60. The body 60 is relatively thin, having two generally flat sides 62, 64, a flat bottom 66, two flat ends 68 with notches 70 therein, and a curved outer surface 72. The radius of curvature of outer surface 72 is the same as that of the disc 22. When the cartridge 54 is plugged into the slot 56 in disc 22, the cartridge outer surface 72 forms a continuation of the periphery of the disc 22, and the handle 58 projects therefrom. Ball detents 74, biased by springs (not shown), hold the cartridge 54 in the disc 22. The disc can be removed by gripping the handle 58, which has two shallow depressions 76 therein, one in each side of the handle, to aid in gripping the handle. A groove 78 is formed in one side 64 only of the cartridge (and not in side 62) and cooperates with a corresponding key 80 (FIG. 5) in the slot 56 to ensure that the cartridge 54 can only be inserted one way into disc 22.

The cartridge 54 includes three circular openings 82-1, 82-2 and 82-3 therein. The centers of openings 82-1 to 82-3 are arranged in an arc 83 (FIG. 2) which is concentric with the outer surface 72, i.e. with the periphery of the disc 22 when the cartridge 54 is plugged into the disc. Each opening 82-1 to 82-3 contains a collector mesh 84-1, 84-2 and 84-3. Since there are three sets of mesh, three sets of collected material will be obtained simultaneously, for three separate later analyses.

The cartridge 54 is formed in two halves from molded plastic, as best shown by the parting line 86 in FIG. 3 and by the half cartridge 54a shown in FIG. 4. The half cartridge 54a of FIG. 4 includes an inwardly projecting peripheral wall 88, thin square outline inwardly projecting ridges 90 encircling each opening 82-1 to 82-3, and small cylindrical female fastener halves 92, having central holes 93. The other half cartridge 54b is identical to the cartridge half 54a, except that instead of the female fastener halves 92 it includes correspondingly located small inwardly projecting plastic pins (not shown) which project with a frictional fit into the holes 93 in the female fastener halves 92, to hold the two cartridge halves together. In addition the half cartridge 54b has the groove 78 formed therein.

Figure 6:
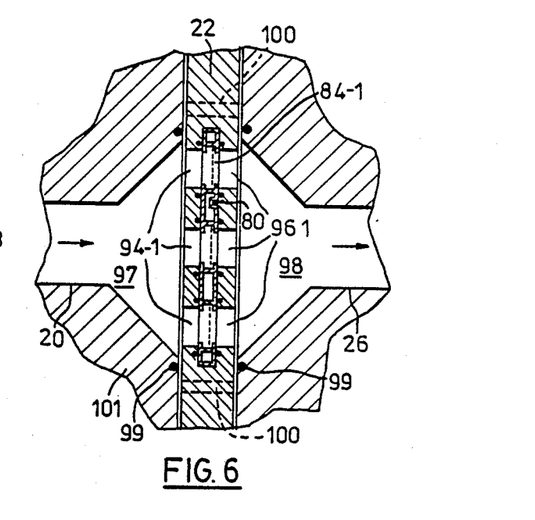
FIG. 6 is a sectional view of the disc, cartridge and associated conduits of FIG. 1.

When the cartridge is being assembled, mesh squares are placed as shown in dotted lines at 84-1, 84-2, 84-3 in FIG. 4, over each square outline ridge 90. Then, when the cartridge halves are forced together, each square of mesh is trapped securely between the ridges 90, as also shown in FIG. 6. The materials of the mesh will be described shortly.

The slot 56 in disc 22 has (see FIG. 5) three openings 94-1, 94-2, 94-3 in one side thereof to admit air from conduit 20 to the meshes 84-1 to 84-3 respectively. The slot 56 also has three opposed openings 96-1, 96-2, 96-3 to allow the air passing through each mesh to enter conduit 26. Each conduit 20, 26 flares outwardly, as shown at 97, 98 in FIG. 6, where it contacts the disc 22, to deliver air evenly and receive air evenly from all three meshes. The gap between disc 22 and the conduits 20, 26 is made small to reduce air leakage, and O-rings 99 are used to seal the gaps between the cartridge and disc, and between the disc 22 and the block 101 in which conduits 20, 26 are located.

As best shown in FIG. 2, the disc 22 has further holes 100 spaced around its periphery in a circular pattern. Holes 100 are of the same diameter as openings 94-1 to 94-3 and 96-1 to 96-3, are spaced apart circumferentially by the same distance as those holes, and have the same radial distance from the disc center as those holes. The purpose of holes 100 will be described shortly.

When the collected material in the meshes 84-1 to 84-3 is to be analyzed, the disc 22 is rotated, e.g. by motor 24, to a position in which the cartridge, now shown at 54' in FIG. 1, is aligned with a further conduit 102. Conduit 102 is of narrow diameter and aligns with one only of the holes 94-1, 94-2 or 94-3 at a time. Conduit 102 is connected to an oven 106. Oven 106 is in turn connected through a solenoid valve 104 to a pressurized source 108 of clean air (from which hydrocarbons and other impurities have been removed). Air from the oven can travel through conduit 102, through one of the meshes 84-1 to 84-3, and then through a transfer line or conduit 110 to the inlet section 38 of analyzer 36. Conduit 110 is also of narrow diameter so that it aligns with one only of holes 96-1 to 96-3 at a time. Conduit 110 is of course across disc 22 from conduit 102 to receive air therefrom when solenoid valve 104 is operated.

Figure 7:
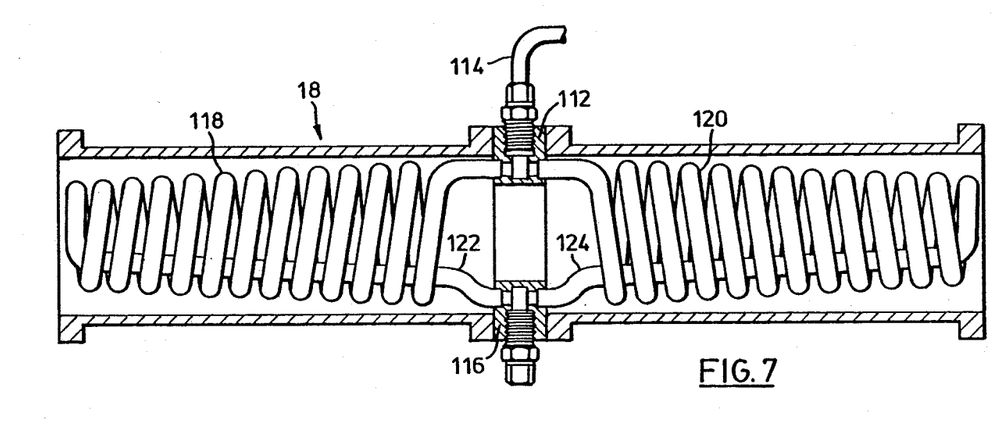
FIG. 7 is a sectional view of a chiller of the FIG. 1 apparatus.
Figure 8:
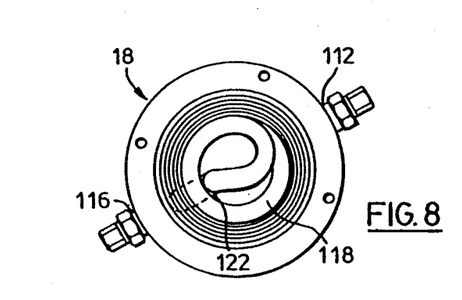
FIG. 8 is an end view of the chiller of FIG. 7.

The chiller 18 is best shown in FIGS. 7 and 8. As shown, the chiller 18 includes an inlet T-fitting 112 which receive refrigerant via a conduit 114, an outlet T-fitting 116 from which refrigerant is withdrawn, and two spiral cooling coils 118, 120 connected to the fittings 112, 116. Coil 118 tapers radially in an upstream direction and coil 120 tapers radially in a downstream direction. In each case, a return line 122, 124 returns refrigerant from the outer end of the coil to fitting 116. The tapered coil configuration (in which each coil turn partially shields the next turn) and the return lines 122, 124 alined with the gas flow direction, reduce the likelihood of particles and low volatility vapours being trapped in the coils while achieving a reasonable degree of cooling efficiency. The coils are also coated with a slippery substance such as TEFLON (trade mark) to reduce adhesion of materials thereto.

In the operation of the apparatus described, the air pump 28 is normally operated continuously. At this time, disc 22 is located so that three of the holes 100 are interposed between conduits 20, 26, and valve 32 is closed. Heated air (at about 45° C. from the inlet conduit 12 then flows continuously through chiller 18 (which is not operated at this time), through holes 100, and through air pump 28. The heated air flowing through chiller 18 tends to remove any particles and low volatility vapours which have been trapped in the chiller.

When sample collection is to occur, the refrigerant is directed to the chiller 18 to operate it. After the chiller 18 has operated for about five seconds, the disc 22 is rotated to align the three meshes of cartridge 54 with conduit 20, and bypass valve 32 is opened. It is assumed that the inlet conduit 12 is now receiving air from a location of interest. A small portion (about 10%) of the sample air is fed through valve 32 and through the bypass conduit 30 into the analyzer inlet section 38 for real time analysis. Valve 34 is connected in parallel with valve 32 and operates at the same time to allow air to leave the analyzer inlet section 38 via the air pump 28 (thus permitting air flow from conduit 30 to enter the inlet section). Most of the sample air passes through meshes 84-1, 84-2 and 84-3, which collect particulates and low volatility vapours therefrom while real time analysis of high volatility vapours is occurring.

The cooling of the sample air before it passes through meshes 84-1 to 84-3 during sample collection is found to increase the collection efficiency substantially. In tests where the chiller 18 cooled the air passing through the meshes from 45° C. initially to about 25° C. as it passed through the meshes, the collection efficiency for low volatility vapours increased by about 2½ times, and yet the passage of particulates through the chiller was not significantly impeded. Ideally the cooling should be to just above the dew point, but not below the dew point since water condensation on the mesh would be undesirable. After sample collection, the chiller is turned off for the remainder of the cycle (which remainder may be about two to four minutes) to allow warm air to flush it out.

After sample collection (and real time analysis) have continued for about 50 to 60 seconds valve 32 is operated to shut off air from bypass conduit 30, ending the real time analysis. The analyzer outlet valve 34 also closes at this time. At the same time, disc 22 is rotated to move the cartridge to its position 54' in FIG. 1, so that mesh 84-1 is aligned with conduits 102, 110. Sample collection has now ended and collected sample analysis can begin. In the meanwhile, warm air continues to flow into chiller 18 (the cooling of which has now been stopped) and through holes 100 to the air pump 28.

Once the cartridge is in position 54' in FIG. 1, valve 104 is operated to allow a short pulse of hot air, typically for about six seconds, to travel from the oven 106 through mesh 84-1 and through transfer conduit 110 into the analyzer 36 for analysis. (The small permanent outlet conduit 35 in the analyzer inlet section 38 is sufficient to allow a flow equal to or slightly greater than this small flow of air to leave the inlet section 38 and be carried to the air pump. This conduit also removes curtain gas entering the inlet section 38.) The hot air evaporates particulates of interest, e.g. drugs or explosives, and low volatility vapours, which have been trapped in mesh 84-1. The volatiles so released move in a pulse along conduit 110 into the analyzer inlet section 36. Because the thermal mass of the mesh 84-1 is very small, it heats quickly so that a large concentration effect is achieved. Although the flow of hot air from oven 106 continues for about six seconds, most of the particulates are vaporized and the low volatility vapours are released in the first second of flow. The remaining five seconds flow of hot air primarily functions to clean the conduit 110, in preparation for reading the contents of the next mesh 84-2.

The oven temperature is normally kept quite high, e.g. at about 500° C., since there are substantial heat losses by the time the air reaches the mesh. The precise initial temperature of the hot air pulse at the mesh is not known, but the steady state temperature with continuous flow of hot air from the oven 106 was about 250° C. Too low a temperature will be inadequate to vaporize particulates of some compounds, particularly drugs, and too high a temperature will break down the compounds, resulting in less vapour of interest for analysis.

The air flow from the oven was typically about 1.9 liters per minute. If most of the particulates were vaporized and low volatility volatiles released in about one second, then the volume of air containing vaporized particulates and low volatility volatiles released from the mesh 84-1 was about 1/30 of a liter. Conversely, the air flow through chiller 18 was approximately 600 liters per minute, divided among three sets of mesh, so that the total volume of air flowing through mesh 84-1 and from which particulates were collected was approximately 200 liters. Therefore a substantial concentration was effected even though the collection efficiency was of course much less than 100%. The sharp high intensity signal which occurs when the sample is rapidly released improves the signal to noise ratio significantly. (Induction or laser heating could also be used, but the method described was inexpensive and effective.)

Each collector mesh 84-1 to 84-3 can be arranged with several screens in series. More screens in series will provide greater collection efficiency, but will also increase the pressure drop as the air flows therethrough. In addition it is more difficult to desorb the screens quickly because of their increased mass. It was found that 2 to 3 screens was the best compromise. The screens or mesh were simply placed as a loose pair, one above the other, over the ridges 90 (FIG. 4) of one cartridge half, and then the other cartridge half was pressed thereon. This held them firmly in position. The use of two screens in series to form each mesh 84-1 to 84-3 is depicted in FIG. 6. In a preferred embodiment, each opening 94-1 to 94-3 and 96-1 to 96-3 was about 0.625 inches in diameter, to handle a flow of about 200 liters per minute through each mesh.

After the contents of mesh 84-1 have been analyzed, the disc 22 is rotated to align mesh 84-2 with conduits 104, 110 and the process is repeated. The process is then again repeated for mesh 84-3. After the cartridge 54 has been fully analyzed, it is thrown away. A new cartridge 54 is then inserted in slot 56 for a new collection and analysis.

The nature of the mesh 84-1 to 84-3 will next be described. Firstly, it was noted that the materials of interest to be analyzed included the following:

| Material | Molecular Weight (in AMU) |
| --- | --- |
| High Volatility Vapours: | |
| acetone | 58 |
| acetic acid | 60 |
| ethyl alcohol | 46 |
| Explosives: | |
| EGDN (ethylene glycol dinitrate) | 152 |
| DNT | 182 |
| TNT | 227 |
| Nitroglycerine | 227 |
| RDX | 222 |
| PETN | 316 |
| Drugs: | |
| THC (tetrahydrocannabinol) | 314 |
| cocaine | 303 |
| heroin | 369 |
| lidocaine | 234 |
| procaine | 236 |
| methamphetamine (typical) | 149 |

Materials of molecular weight below 100, e.g. acetone, usually have a high vapour pressure and cannot normally be trapped on a mesh so they must be read in real time. Materials of molecular weight between 100 and 200 in some cases can be trapped on a mesh, if they have a sufficiently low vapour pressure, but they tend to evaporate rapidly therefrom. For example, the explosive EGDN (molecular weight 152) can be read in real time or trapped on a mesh, but it will evaporate from the mesh in about 60 seconds at room temperature, so it is best to analyze it in real time. However as the molecular weight increases, the vapour pressure decreases, and because of the low concentrations available it becomes increasingly difficult to analyze the material in real time and increasingly easy to trap it on a mesh to enhance the signal. For example the explosive DNT (molecular weight 182) can be read either in real time or after collection in a mesh, but provided that the mesh is desorbed within about 60 seconds after collection, the signal enhancement by collecting it on a mesh (as compared with real time analysis) is a factor of 3 or 4. At the heavier end of the spectrum, compounds such as heroin (molecular weight 369) rarely appear in anything but particulate form.

With this in mind, several materials were tried for use as mesh material. It was found that stainless steel, bronze and nickel worked well with most compounds of interest (drugs and explosives). Because of its low cost and ready availability, a bronze mesh was selected. Specifically, the mesh was phosphor bronze, although it contains little phosphor (usually less than 0.2%), and was in fact 90% copper, 6 to 9% tin, and 1 to 4% lead (only components above 1% are listed). A low mass fine mesh was found best, typically 300 to 400 mesh. A 325 mesh phosphor bronze mesh was finally selected, wire diameter 0.0014 inches.

Numerous treatments of the mesh surface were tested. The objective, initially, was to increase the chemical binding ability of the screen, and to increase its surface area without significantly increasing its physical dimensions or mass. It was at first considered desirable to enhance the low volatility vapour collection efficiency of the mesh without sacrificing its inherent ability to collect particles by mechanical trapping. Treatments such as silicone oils, silicone oils followed by heating, charcoal coating, in situ generation of charcoal coating, surface etching with acids, bases and oxidizing compounds, mechanical surface roughening (by sand and abrasives), and metallic coatings by vacuum deposition and electroplating were all tested. The only highly useful treatment was found to be electroplating of a specific nature. As will be explained, the electroplating was found useful for trapping low volatility explosive vapours, but not for trapping drug compounds.

Various metals were electroplated onto the mesh and tested. Metals such as tungsten (by evaporation), platinum, iridium, gold, silver, copper, nickel, zinc, chromium, cobalt and palladium were tested. It was found that a number of metals increased the ability of the mesh to collect vapours, but only when plated in certain ways. Different electroplating techniques were tested, including varying the acidity of the plating solution, the concentration thereof, the current density, solution additives, precleaning prior to plating, plating bath geometry (electrode type and location), and commercial standard electroplating. It was found that the most useful plating technique which enhanced the ability of the mesh to adsorb vapours, produced a very rough and grainy metallic coating. Commercial electroplating produced a smooth coating which did not significantly enhance the vapour collection properties of the screen. It was found that zinc, nickel and platinum were all highly suitable as electroplating metals for the applications of interest (namely trapping explosives volatiles). However zinc was selected because of its low cost and ease of electroplating.

Figure 9:
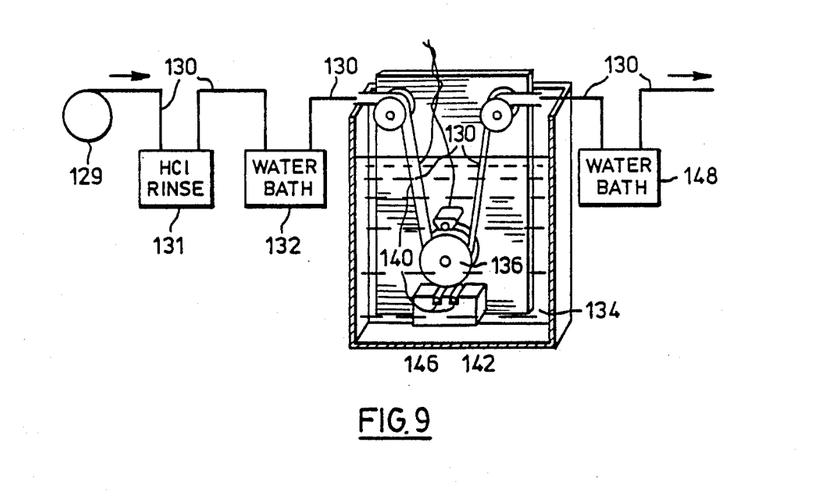
FIG. 9 is a diagrammatic view of electroplating apparatus.

The electroplating was carried out as indicated diagrammatically in FIG. 9. A roll 129 of phosphor bronze mesh 130 as described was provided, and was first cleaned, e.g. in a 50% hydrochloric acid solution 131, then rinsed in a tap water bath 132, and then run through a container 133 containing a plating bath 134. The bath 134 consisted of a 5% (weight to volume)

solution of zinc chloride. The mesh 130 was directed over a spool 136 rotatably mounted on a plastic plate 138. Plastic blocks 140, 142 were fixed to plate 138 above and below spool 136, and projecting outwardly in close proximity to the spool. Each block carried a platinum wire anode 144, 146 respectively, located in grooves in the blocks. The anodes 144, 146 were located close to the ribbon of mesh 130 to keep the voltage as low as possible while maintaining a relatively high current density of about 0.2 amps/cm$^2$. Each area of mesh was exposed to the current for about 10 seconds. After being plated the mesh was washed in a tap water bath 148 and dried with hot air at about 70° C.

Although a cyanide catalyst is normally used in zinc electroplating, in this case no catalyst and indeed no additives were used. The solution was thus highly acidic, with a pH of about 2. The resulting electroplated surface was rough and highly fissured.

Figure 10:
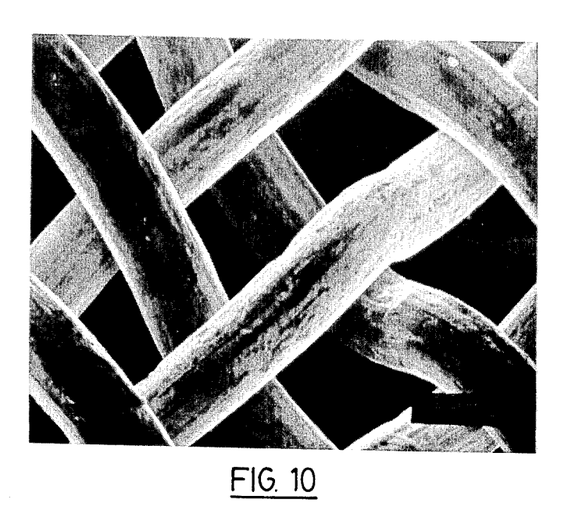
FIGS. 10 and 11 are micrographs of untreated wire mesh used in the FIG. 1 apparatus, to two different scales.
Figure 11:
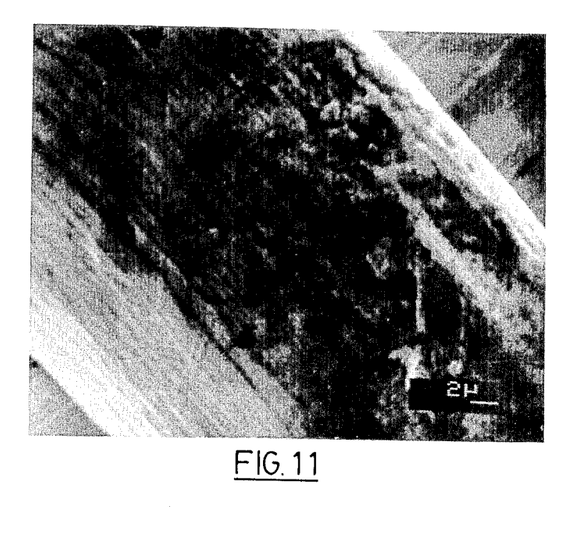

In particular, reference is made to FIGS. 10 and 11, which are the electron micrographs showing the phosphor bronze mesh before treatment. The scale of each photograph is shown by a small scale bar therein. In FIG. 10 the scale bar is 10 microns long (1 micron=0.001 mm) and in FIG. 11 the scale bar is 2 microns long. It will be seen that the phosphor bronze surface is relatively smooth.

Figure 12:
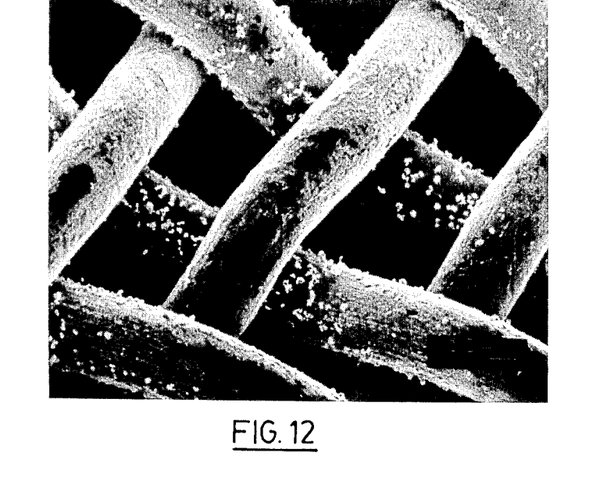
FIG. 12 is a micrograph of the wire mesh of FIGS. 10 and 11 after having been electroplated according to the invention.
Figure 13:
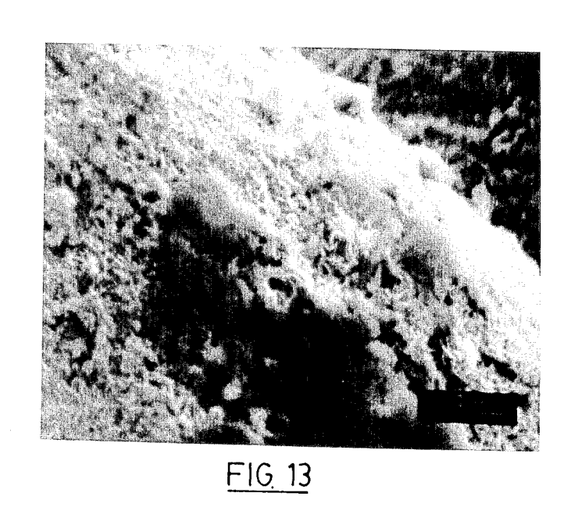
FIGS. 13 and 14 are micrographs from different angles of the FIG. 12 mesh at a greater magnification.
Figure 14:
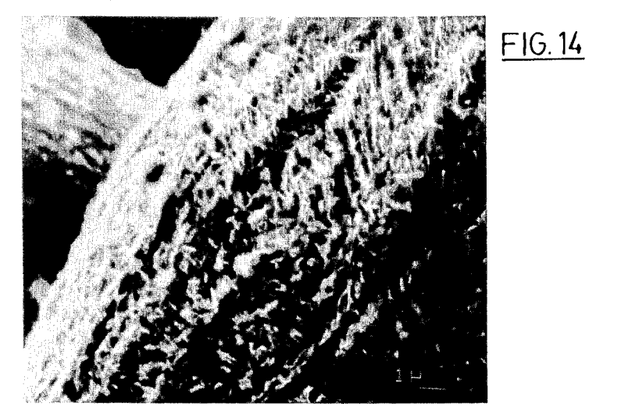

FIGS. 12, 13 and 14 show electron micrographs of the mesh after zinc electroplating according to the process described. The scale bars for these figures are 10, 1 and 1 micron respectively. The zinc plated surfaces are roughened even in the 10 micron view, and have great surface roughness and numerous fissures in the 1 micron views. The roughness was not of a kind having large surface features (like mountains) but was of a kind having a very large number of valleys, ridges and surface discontinuities or fissures. Such plating tended to rub off much more easily with abrasion than commercial plating. However the surface roughness and defects greatly improved the trapping of vapours. (In some cases, e.g. for nitroglycerine, the enhancement was by a factor of about five to eight.)

It was found, surprisingly, that although the zinc plated bronze mesh worked well for most explosives vapours, it did not work well for drug vapours. It was found, in fact, that the signal received from a zinc electroplated bronze mesh was only 1/5 to 1/6 of that received from an untreated bronze mesh, when drug particles were collected on each. It appeared, although the precise reasons are not known with certainty, that this was because as soon as the pulse of hot air from oven 106 vaporized the drug particles, the zinc catalyzed a reaction which decomposed much of the hot drug vapour. Most drugs (which are alkaloids) behaved in the same manner.

Figure 15:
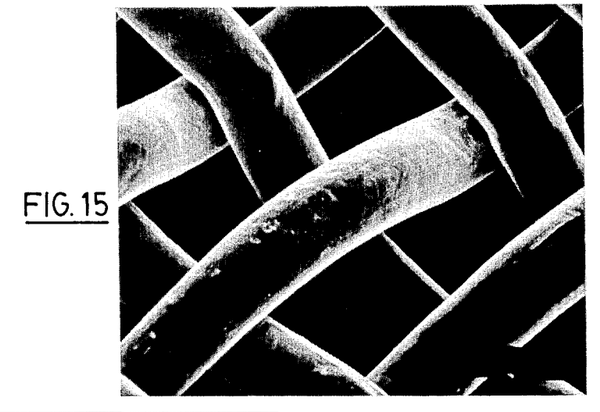
FIGS. 15 and 16 are micrographs to different scales of the wire mesh of FIGS. 10 and 11 but with an oxidized surface.
Figure 16:
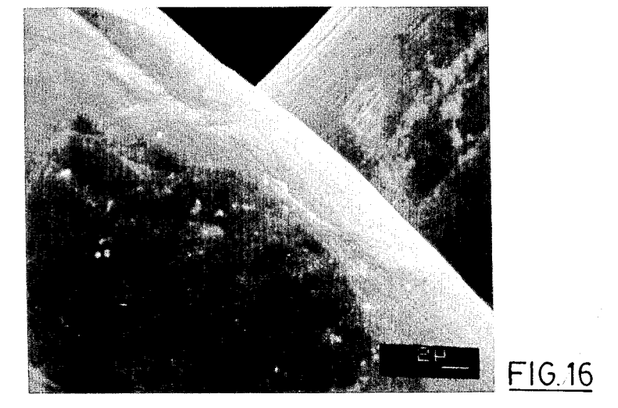

Therefore, to improve the collection and release of drugs without adverse reactions, phosphor bronze mesh of the kind described was passed through an oven at a temperature of about 280° C. with a residence time therein of about 20 seconds. This treatment oxidized the surface of the phosphor bronze mesh, and rendered it less reactive. FIGS. 15 and 16 are electron micrographs of the oxidized phosphor bronze mesh, with scale bars of 10 and 2 microns respectively. It will be seen that the surface is quite smooth, and it is of course relatively inert. It was found that this treatment increased the sensitivity for heroin by a factor of about five as compared with untreated phosphor bronze mesh. For other drugs the improvement was less, but in no case was the sensitivity reduced.

The mesh 84-1 is therefore typically of phosphor bronze having an oxidized surface, as discussed. The meshes 84-2 and 84-3 are both typically phosphor bronze electroplated with zinc in the manner described. Analysis of mesh 84-1 will therefore typically detect drugs. Analysis of meshes 84-2 and 84-3 will typically detect explosives. Two identical meshes 84-2 and 84-3 are provided so that the contents of one mesh 82-2 can be analysed by ionizing the gas therefrom directly in inlet section 38, and the contents of the other mesh 82-3 can be ionized in the presence of a chemical reagent gas. Such an arrangement as shown in FIG. 1, where a source 150 of chemical reagent gas is shown, connected to conduit 34 by a valve 152 and conduit 154. When the mesh 82-3 is to be desorbed, valve 152 is opened to allow a pulse of chemical reagent gas to mix with the gas from the mesh 82-3. The two different methods of analysis help to provide more accurate detection of explosives with a lower rate of false alarms.

Figure 17:
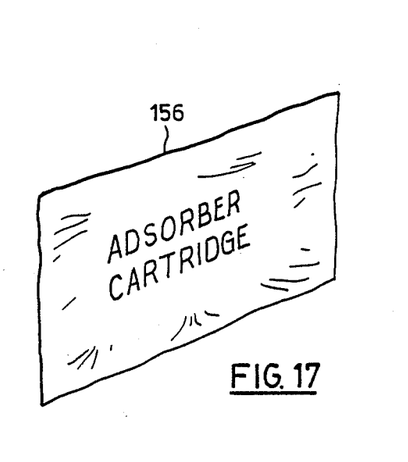
FIG. 17 is a diagrammatic view of a foil pouch for containing a cartridge of the invention.

The cartridges of the invention are versatile in their use. Each cartridge 54 is normally packaged in a sealed aluminum foil pouch, as indicated diagrammatically at 156 in FIG. 17. When the pouch 156 is opened, the cartridge must normally be used fairly promptly. Once it has collected particles and vapours, most collected particles will be retained on the collector cartridges for substantial time. Low volatility vapours are usually retained for at least about 10 minutes (for 10% loss), although as discussed previously this varies with the vapour in question. The retention time can be increased by refrigerating the cartridges.

The meshes 84-1 to 84-3 in the cartridge should be spaced far enough apart so that one can be desorbed without affecting the other. A separation of about 0.5 inches is more than sufficient. The plastic of the cartridge 54 should be non-conductive thermally and should be of low molecular weight, so as not to affect readings. Polypropylene without plasticizers has been found to be a suitable plastic for the cartridge body.

Instead of being used in the disc 22 as described, the cartridges 54 can be used in a hand held collector gun which will draw air through them for a predetermined period of time. The cartridges after being used in this way must either be refrigerated for later analysis or else analyzed quickly (within one to ten minutes). They may also be used passively, e.g. in a duct of an aircraft air conditioning system, and then removed for analysis.

It will be seen that the apparatus described provides a number of channels for collection and analysis, namely a real time channel, and at the same time several different collection channels which are of differing selectivity. Normally at least one of the channels is adapted for high sensitivity to particulates (e.g. of drugs), and at least one channel has high sensitivity to explosives. The collector channels or meshes are thus said to be of different selectivity, i.e. one selects (traps and releases with limited decomposition) one chemical class (drug particulates), and responds less well to other chemical classes (explosives vapours), and the other selects oppositely to the first.

We claim:
1. Apparatus for collecting and analyzing trace substances, said apparatus comprising inlet means for receiving a stream of warm gas containing particulates and low volatility vapours of said trace substances, collection means connected to said inlet means for col- lecting said trace substances, cooling means located between said inlet means and said collection means for cooling said warm air flowing from said inlet means said collection means, thereby to increase the efficiency of collection of said collection means, analyzer means for analyzing said trace substances, bypass conduit means extending between said inlet means and said analyzer means to direct a portion of said stream of warm gas to said analyzer means, and control means for controlling said analyzer to analyze said portion of said stream of warm gas simultaneously with the collection of trace substances at said collection means.

2. Apparatus according to claim 1 wherein said collection means comprises first and second collectors, one of said collectors having greater selectivity than the other for one chemical class and the other collector having greater selectivity for another chemical class than said one collector.

3. Apparatus according to claim 2 wherein said one collector is a lightweight fine metal mesh having an oxidized surface to decrease the reactivity thereof.

4. Apparatus according to claim 3 wherein said metal is phosphor bronze.

5. Apparatus according to claim 2 wherein said other collector is a lightweight fine mesh of a first metal, said mesh having a second metal electroplated thereon to form a rough fissure filled surface.

6. Apparatus according to claim 5 wherein said second metal is selected from zinc, nickel and platinum.

7. Apparatus according to claim 5 wherein said first metal is phosphor bronze and said second metal is zinc.

8. Apparatus for analyzing trace substances, comprising:
 (a) inlet means for receiving inlet air containing said trace substances,
 (b) first and second collectors each of different selectivity than the other,
 (c) means for directing at least a portion of said inlet air through both said first and second collectors in parallel, for said first and second collectors each simultaneously to collect at least some of said trace substances,
 (d) analyzer means,
 (e) means for first releasing and transporting to said analyzer means the substances collected by said first collector, and thereafter releasing and transporting to said analyzer means the substances collected by said second collector,
 (f) bypass means for directing a fraction of said inlet air to bypass said first and second collectors,
 (g) and means selectivity connecting said bypass means to said analyzer means for analyzing trace substances in said fraction of said air simultaneously with collection of trace substances by said collectors.

9. Apparatus according to claim 8 and including a disposable collector cartridge, said first and second collectors being located in said catridge.

10. Apparatus according to claim 8 wherein each said collector comprises a fine lightweight wire mesh.

11. Apparatus according to claim 8 wherein each said collector comprises a fine lightweight wire mesh, said mesh of said first collector having an oxidized surface to increase its inertness.

12. Apparatus according to claim 8 wherein said mesh of said second collector has a surface having numerous surface fissures and imperfections therein to increase its ability to trap low volatility vapours.

13. Apparatus according to claim 8 wherein the mesh of said second collector means has a metal electroplated thereon to form a rough electroplated surface.

14. Apparatus according to claim 8 and including means for cooling air flowing to said first and second collectors to improve collection thereby.

15. Apparatus according to claim 14 wherein said cooling means includes a refrigerating coil coated with a smooth non-absorbant substance.

16. Apparatus according to claim 9 wherein said means (e) includes means for heating said collector, flow means for producing a gas flow through said collector to remove collected trace substances therefrom, and means selectively connecting said flow means to said analyzer.

17. Apparatus for analyzing trace substances, comprising:
 (a) inlet means for receiving inlet air containing said trace substances,
 (b) first and second collectors each of different selectivity than the other,
 (c) means for directing at least a portion of said inlet air through both said first and second collectors in parallel, for said first and second collectors each simultaneously to collect at least some of said trace substances,
 (d) analyzer means,
 (e) means for first releasing and transporting to said analyzer means the substances collected by said first collector, and thereafter releasing and transporting to said analyzer means the substances collected by said second collector,
 (f) said means (e) including means for heating said collector, flow means for producing a gas flow through said collector to remove collected trace substances therefrom, and means selectively connecting said flow means to said analyzer,
 (g) a disposable collector cartridge, said first and second collectors being located in said cartridge,
 (h) said means (c) including a disc having a central axis, means mounting said disc for rotation about said axis, said disc having a slot in an edge thereof, said slot being adapted to receive said cartridge, at least two orifices each extending through said disc and communicating with said slot each for directing air from said inlet means past one of said collectors in said cartridge and then to a vent, and means for rotating said disc to positions in which first one of said orifices is aligned with said flow means for releasing trace substances from one collector and then the other of said orifices is aligned with said flow means for releasing trace substances from the other collector.

18. A disposable cartridge for collecting trace substances to be analyzed, said cartridge comprising at least two collectors therein, each collector being formed from a lightweight filter material of low thermal mass, a body supporting and retaining said collectors in spaced apart relationship from each other, said body being formed of plastic of low thermal conductivity, said collectors providing at least two channels of different selectivity from each other for simultaneous sample collection, said body is of flat thin form, said body having a first portion containing said collectors and a second and handle portion connected to said first portion, said first portion being adapted to be plugged into a holder for passing air through said collectors, said cartridge being generally T-shaped, said first portion being the stem of said T and said second portion the bar of said T, said collectors being arranged in an arc on said second portion.

19. A cartridge according to claim 18 wherein said mesh of one of said collectors has an oxidized surface to increase its inertness.

20. A disposable cartridge for collecting trace substances to be analyzed, said cartridge comprising at least two collectors therein, each collector being formed from a lightweight wire mesh of low thermal mass, a body supporting and retaining said collectors in spaced apart relationship from each other, said body being formed of plastic of low thermal conductivity, said collectors providing at least two channels of different selectivity from each other for simultaneous sample collection, said mesh of one of said collectors having an oxidized surface to increase its inertness, said mesh of another of said collectors being electroplated with a further metal to form a rough fissure-filled surface.

21. A cartridge according to claim 20 wherein said further metal is zinc.

22. A cartridge according to claim 21 and having at least three collectors therein, one of said collectors being of phosphor bronze mesh having said oxidized surface, and the other two collectors being of phosphor bronze having zinc electroplated thereon to form said rough fissure-filled surface.

23. A method of analyzing trace substances, comprising:
 (a) producing a stream of inlet air containing said trace substances from a target zone of interest,
 (b) directing a first portion of said inlet air in parallel past at least two collectors of different selectivity for different substances in said inlet air,
 (c) simultaneously with said step (b), bypassing a second portion of said inlet air around said collectors and into an analyzer for real time analysis,
 (d) then after said real time analysis, separately heating each of said collectors and analyzing in sequence the trace substances collected by each of said collectors.

24. A method according to claim 23 and including the step of cooling said first portion of said inlet air.

25. Apparatus for analyzing trace substances, comprising:
 (a) inlet means for receiving inlet air containing said trace substances,
 (b) first and second collectors,
 (c) means for directing a portion of said inlet air through both said first and second collectors in parallel, for said first and second collectors each simultaneously to collect some of said trace substances,
 (d) analyzer means,
 (e) means for selectively directing a portion of said inlet air to said analyzer means simultaneously with the passage of said inlet air through said first and second collectors, to permit real time analysis of some of said trace substances simultaneously with collection of some of said trace substances in said collectors,
 (f) and means for first releasing and transporting to said analyzer means, after said real time analysis, the substances collected by said first collector for analysis thereof, and thereafter releasing and transporting to said analyzer means the substances collected by said second collector for analysis thereof.

26. A method of analyzing trace substances, comprising:
 (a) producing a stream of inlet air containing said trace substances from a target zone of interest,
 (b) directing a portion of said inlet air in parallel past at least two collectors to collect in said collectors trace substances in said inlet air,
 (c) simultaneously with said step (b), passing a portion of said inlet air into an analyzer for real time analysis of some of the trace substances in said inlet air,
 (d) then after said real time analysis, separately heating each of said collectors and analyzing in sequence the trace substances collected by each of said collectors.

27. A method according to claim 26 wherein said trace substances are selected from the substances consisting of drugs and explosives.

* * * * *